(12) United States Patent
Xu

(10) Patent No.: US 9,188,561 B2
(45) Date of Patent: Nov. 17, 2015

(54) TEST STRIP

(71) Applicant: Yue Xu, Shanghai (CN)

(72) Inventor: Yue Xu, Shanghai (CN)

(*) Notice: Subject to any disclaimer, the term of this patent is extended or adjusted under 35 U.S.C. 154(b) by 48 days.

(21) Appl. No.: 13/783,376

(22) Filed: Mar. 3, 2013

(65) Prior Publication Data
US 2014/0248694 A1 Sep. 4, 2014

(51) Int. Cl.
G01N 27/00 (2006.01)
G01N 27/327 (2006.01)

(52) U.S. Cl.
CPC .................................. G01N 27/3272 (2013.01)

(58) Field of Classification Search
CPC .................................................. G01N 27/3272
USPC ................................ 422/50, 68.1, 82.01, 420
See application file for complete search history.

(56) References Cited

U.S. PATENT DOCUMENTS

| 7,118,668 | B1* | 10/2006 | Edelbrock et al. | 205/777.5 |
| 7,550,290 | B2* | 6/2009 | Yamamoto | 435/287.8 |
| 7,604,721 | B2* | 10/2009 | Groll et al. | 204/403.01 |
| 2002/0148726 | A1* | 10/2002 | Yamamoto et al. | 204/403.14 |
| 2002/0192115 | A1* | 12/2002 | Bhullar et al. | 422/82.01 |
| 2006/0070878 | A1* | 4/2006 | Wu et al. | 204/403.01 |

* cited by examiner

Primary Examiner — Lyle Alexander
Assistant Examiner — Robert Eom

(57) ABSTRACT

The invention includes a base, a working wire, a grounding wire, a first division layer, a second division layer and a cover layer. The base has a reaction area. The working wire is formed with a first measure contact and a first bioreaction contact. The grounding wire is formed with a second measure contact and a second bioreaction contact. The first division layer and second division layer have a first inlet and a second inlet, respectively. The first inlet and the second inlet correspond to the reaction area in position to expose the first and second bioreaction contacts. The guiding trough is formed by the cover layer, the base and the first and second inlets.

4 Claims, 13 Drawing Sheets

TEST STRIP

BACKGROUND OF THE INVENTION

1. Technical Field

The invention relates to diagnostic instruments, particularly to biological reagents.

2. Related Art

A biosensor is an analytical device, used for the detection of an analyte, that combines a biological component with a physicochemical detector. A common example of a commercial biosensor is the blood glucose biosensor, which uses the enzyme glucose oxidase to break blood glucose down. In doing so it first oxidizes glucose and uses two electrons to reduce the FAD (a component of the enzyme) to FADH2. This in turn is oxidized by the electrode (accepting two electrons from the electrode) in a number of steps. The resulting current is a measure of the concentration of glucose. In this case, the electrode is the transducer and the enzyme is the biologically active component.

For the sake of portability or home use, compact biosensors using disposable test strips appear in the market and are extensively used. Different types of test strips may have a similar or the same shape or appearance. Users must visually distinguish and confirm the compatibility between a biosensor and a test strip. It is possible that an incompatible test strip is misapplied in a biosensor. There must be a risk of misapplying an incompatible test strip. This is a really serious problem for users or patients.

SUMMARY OF THE INVENTION

An object of the invention is to provide a test strip which can be electrically distinguished by a biosensor (such as a blood glucose meter) to prevent an incompatible test strip from being misapplied.

To accomplish the above object, the test strip of the invention includes a base, a working wire, a grounding wire, a first division layer, a second division layer and a cover layer. The base has a reaction area. The working wire is formed on the base. Two ends of the working wire are separately formed with a first measure contact and a first bioreaction contact. The first bioreaction contact extends into the reaction area. The grounding wire is formed on the base and is parallel to the working wire. Two ends of the grounding wire are separately formed with a second measure contact and a second bioreaction contact. The second bioreaction contact extends into the reaction area. The first division layer has a first inlet. The second division layer has a second inlet and is superposed on the first division layer and overlapped with the working wire and the grounding wire. The first inlet and the second inlet correspond to the reaction area in position to expose the first and second bioreaction contacts. The cover layer is attached on the second division layer. A guiding trough is formed by the cover layer, the base and the first and second inlets.

DETAILED DESCRIPTION OF THE INVENTION

Figure 1:
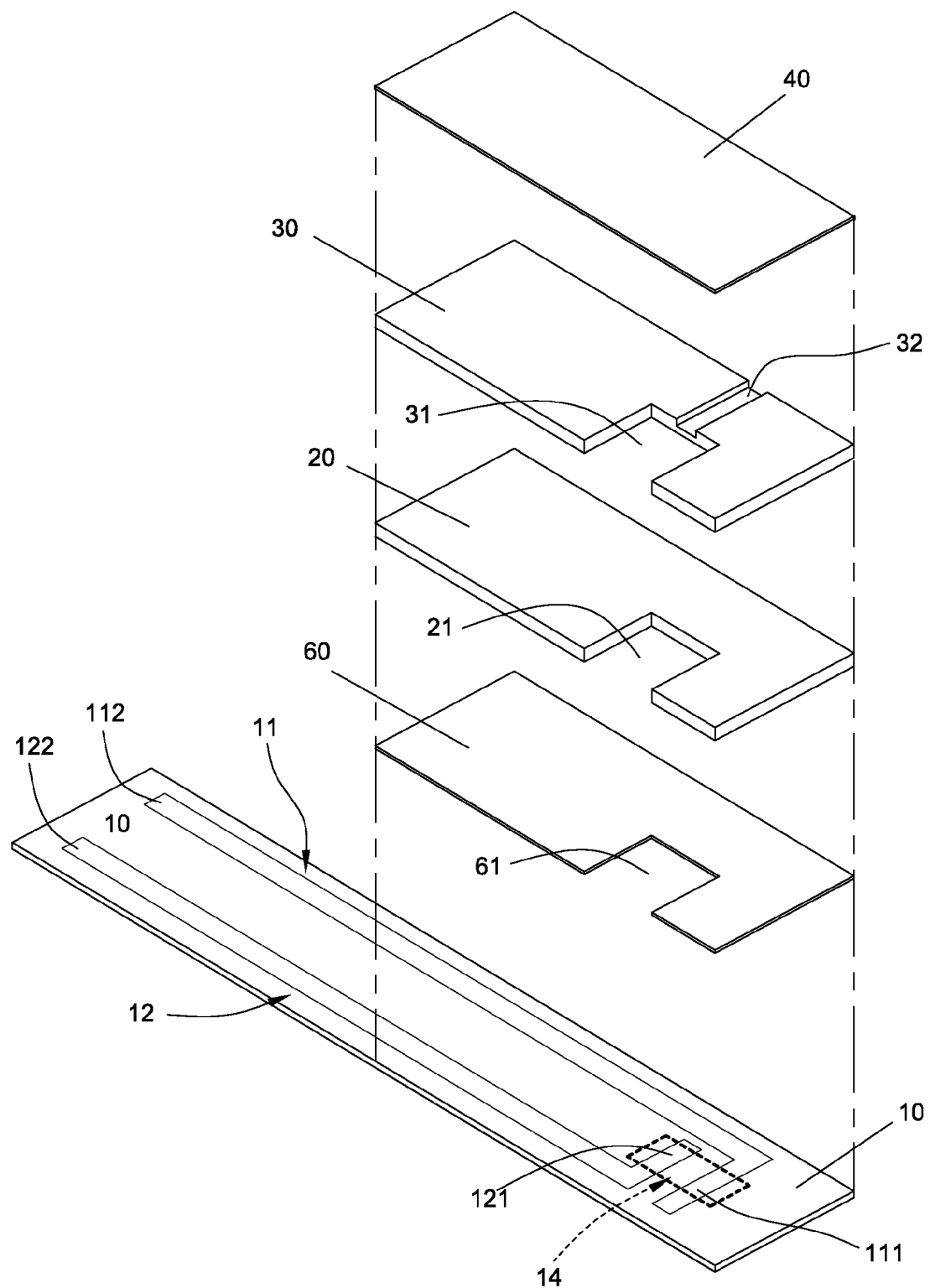
FIG. 1 is an exploded view of the first embodiment of the invention.
Figure 2:
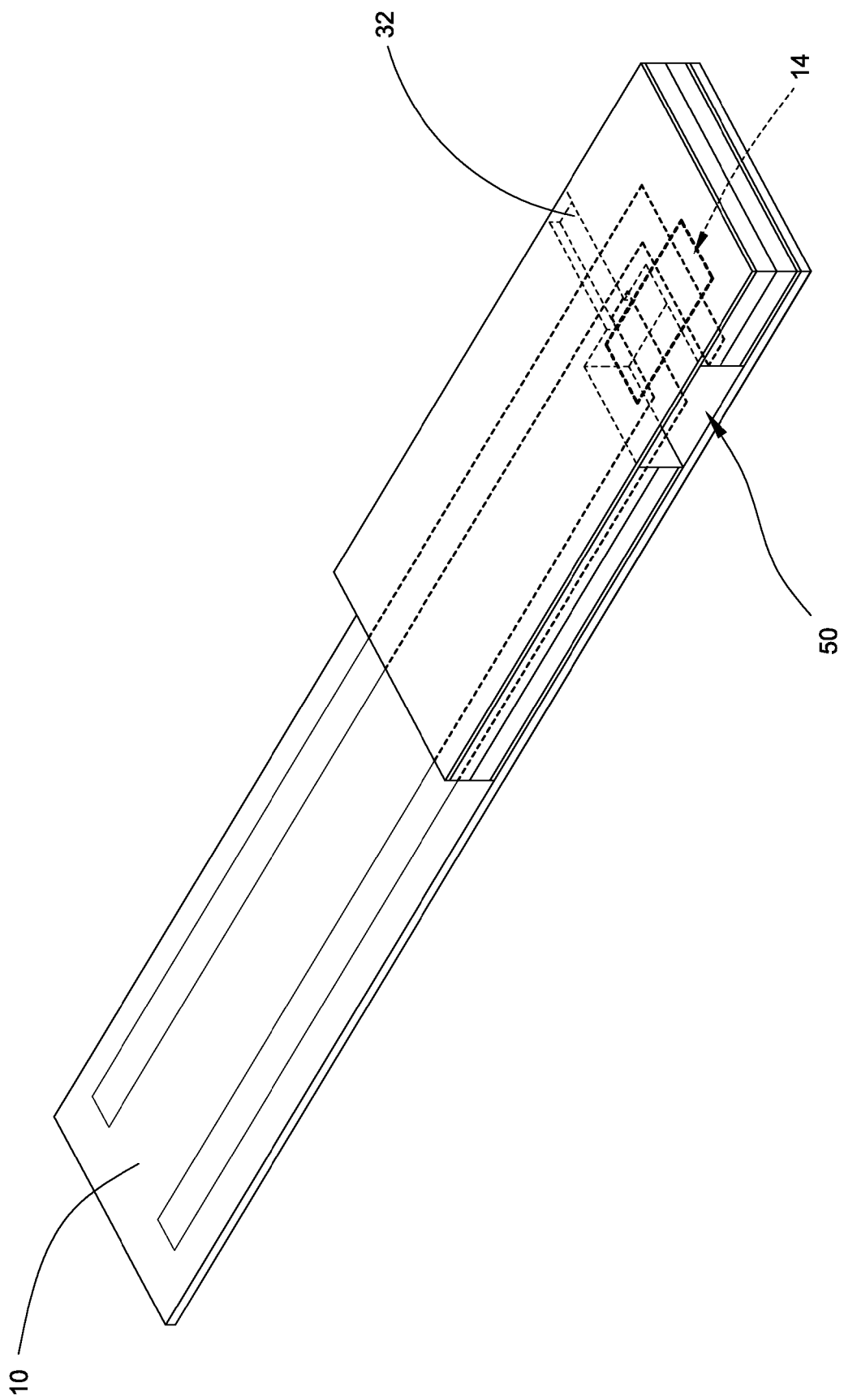
FIG. 2 is an assembled view of the first embodiment of the invention.
Figure 3:
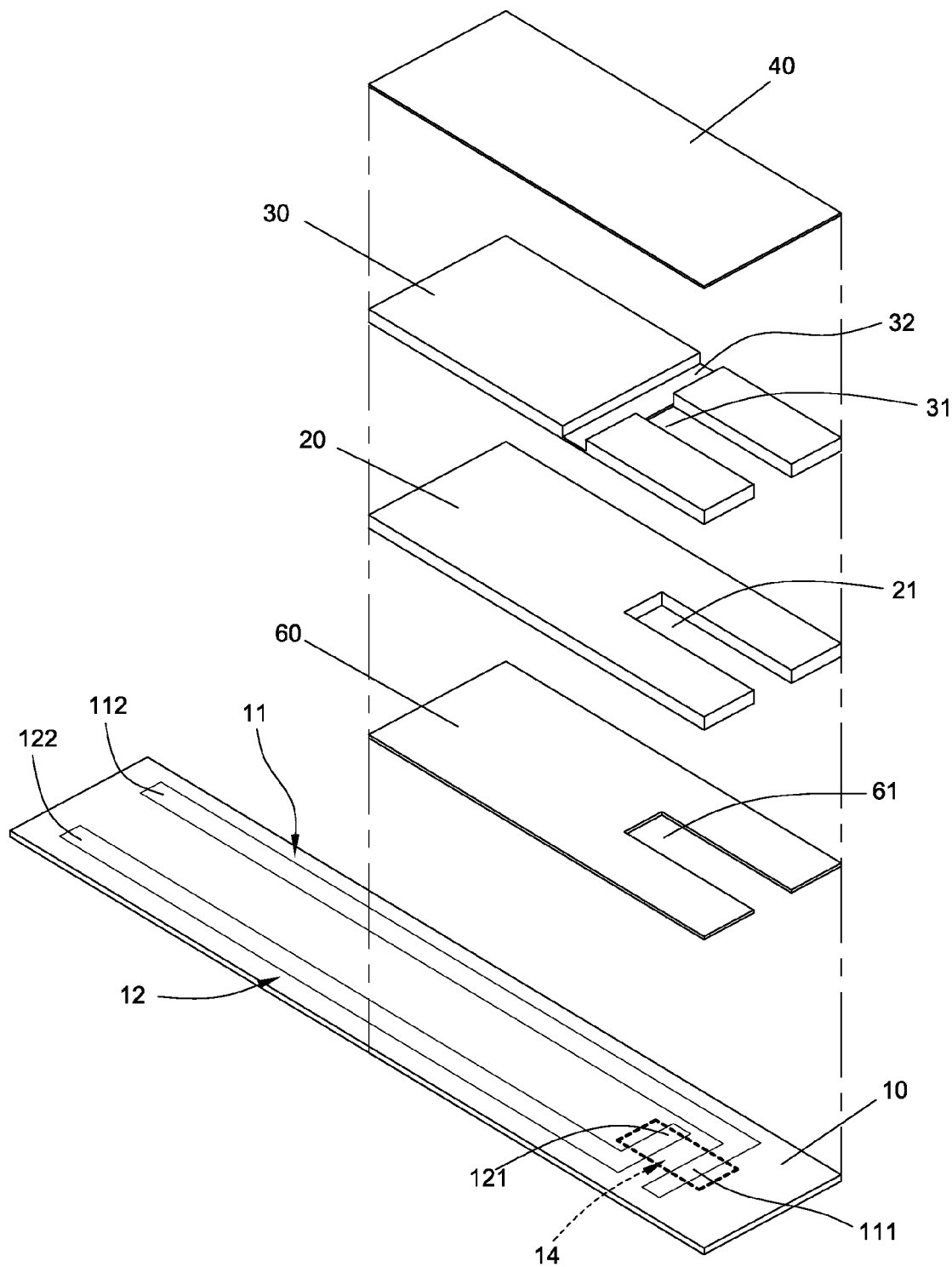
FIG. 3 is an exploded view of the second embodiment of the invention.

Please refer to FIGS. 1 and 2, which show the first embodiment of the invention. The test strip of the invention includes a base 10, a working wire 11, a grounding wire 12, a first division layer 20, a second division layer 30 and a cover layer 40. The base 10 is defined with a reaction area 14. The working wire 11 and the grounding wire 12 are parallelly formed on the base 10. Two ends of the working wire 11 are separately formed with a first measure contact 112 for connecting an external biosensor and a first bioreaction contact 111. The first bioreaction contact 111 extends into the reaction area 14. The grounding wire 12 is parallel to the working wire 11. Two ends of the grounding wire 12 are separately formed with a second measure contact 122 for connecting the external biosensor and a second bioreaction contact 121. The second bioreaction contact 121 extends into the reaction area 14. The first division layer 20 is provided with a first inlet 21 on a side thereof. The second division layer 30 is provided with a second inlet 31. The second division layer 30 is superposed on the first division layer 20 and overlapped with the working wire 11 and the grounding wire 12. The first inlet 21 and the second inlet 31 correspond to the reaction area 14 in position to expose the first and second bioreaction contacts 111, 121. The cover layer 40 is attached on the second division layer 30. A guiding trough 50 is formed by the cover layer 40, the base 10 and the first and second inlets 21, 31.

The reaction area 14 is coated with at least one bioreaction film (such as an enzyme or chemical reagent). A specimen can be introduced into the reaction area 14 through the guiding trough 50 and spread on the first and second bioreaction contacts 111, 121 and the bioreaction film thereon. As a result, a biological detection based on bioelectricity can be obtained. Furthermore, an adhesive layer 60 is disposed between the first division layer 20 and the base 10, and the adhesive layer 60 is formed with a recess 61 corresponding to the first inlet 21. The adhesive layer is made of polyethylene terephthalate (PET).

Figure 4:
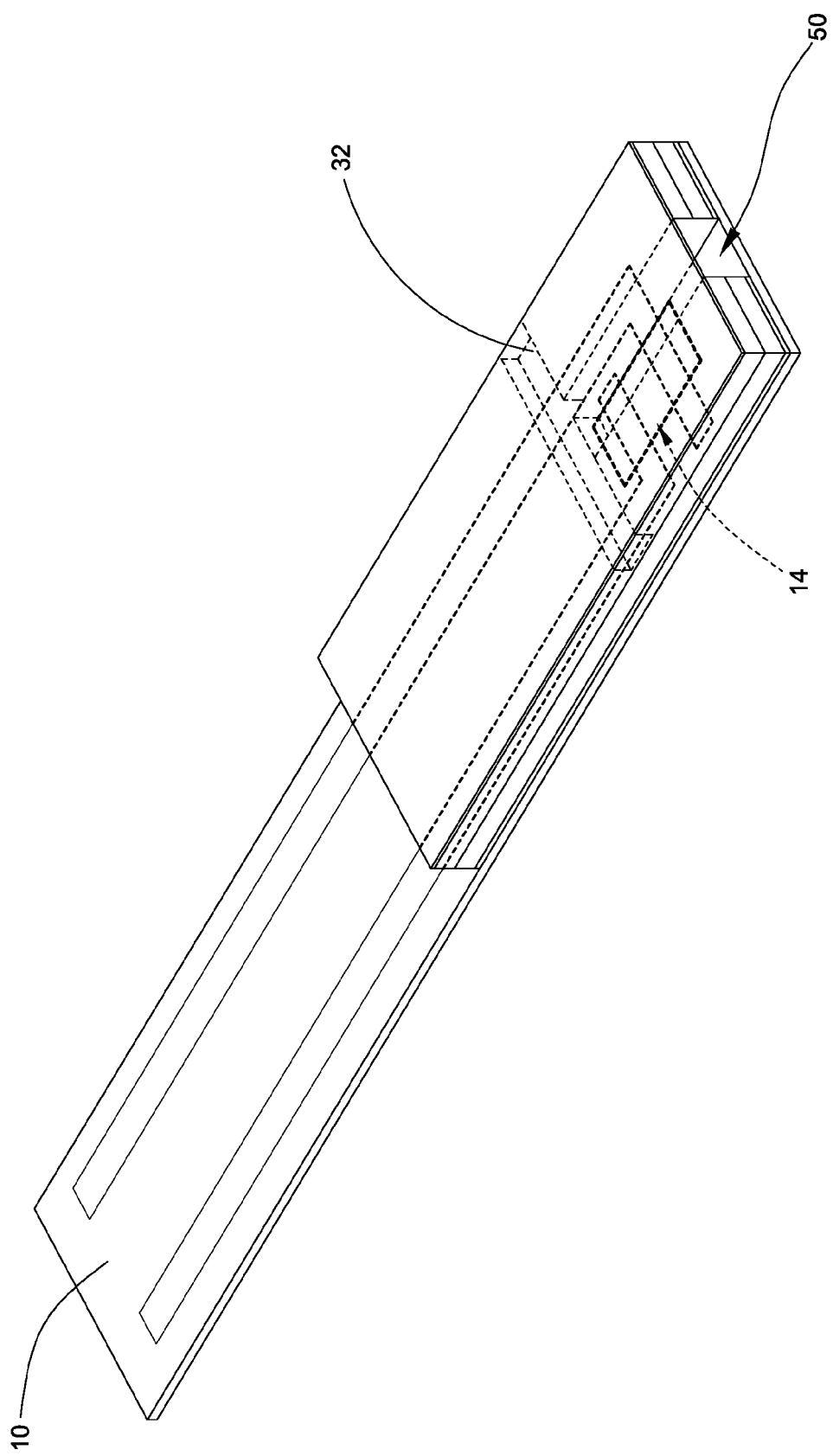
FIG. 4 is an assembled view of the second embodiment of the invention.

As shown in FIGS. 2 and 4, an end of the first inlet 21 is further formed with an air passage 32. The air passage 32 communicates with the first inlet 21 to promote the specimen in the guiding trough 50 to flow.

In the embodiment shown in FIG. 2, the air passage 32 is perpendicular to the first inlet 21. In the embodiment shown in FIG. 4, the air passage 32 is parallel to the first inlet 21.

Figure 5:
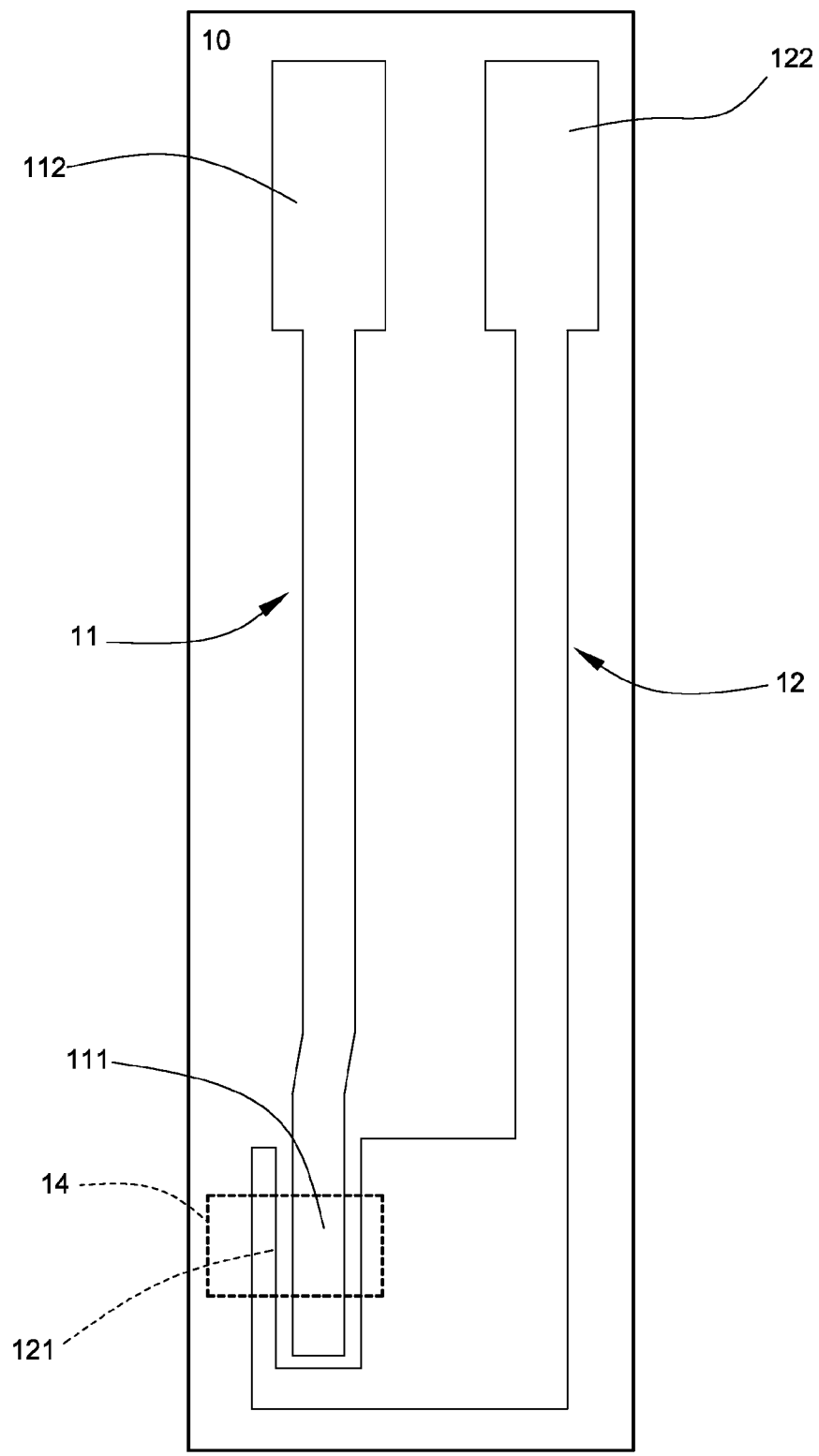
FIG. 5 shows an arrangement of the wires.
Figure 6:
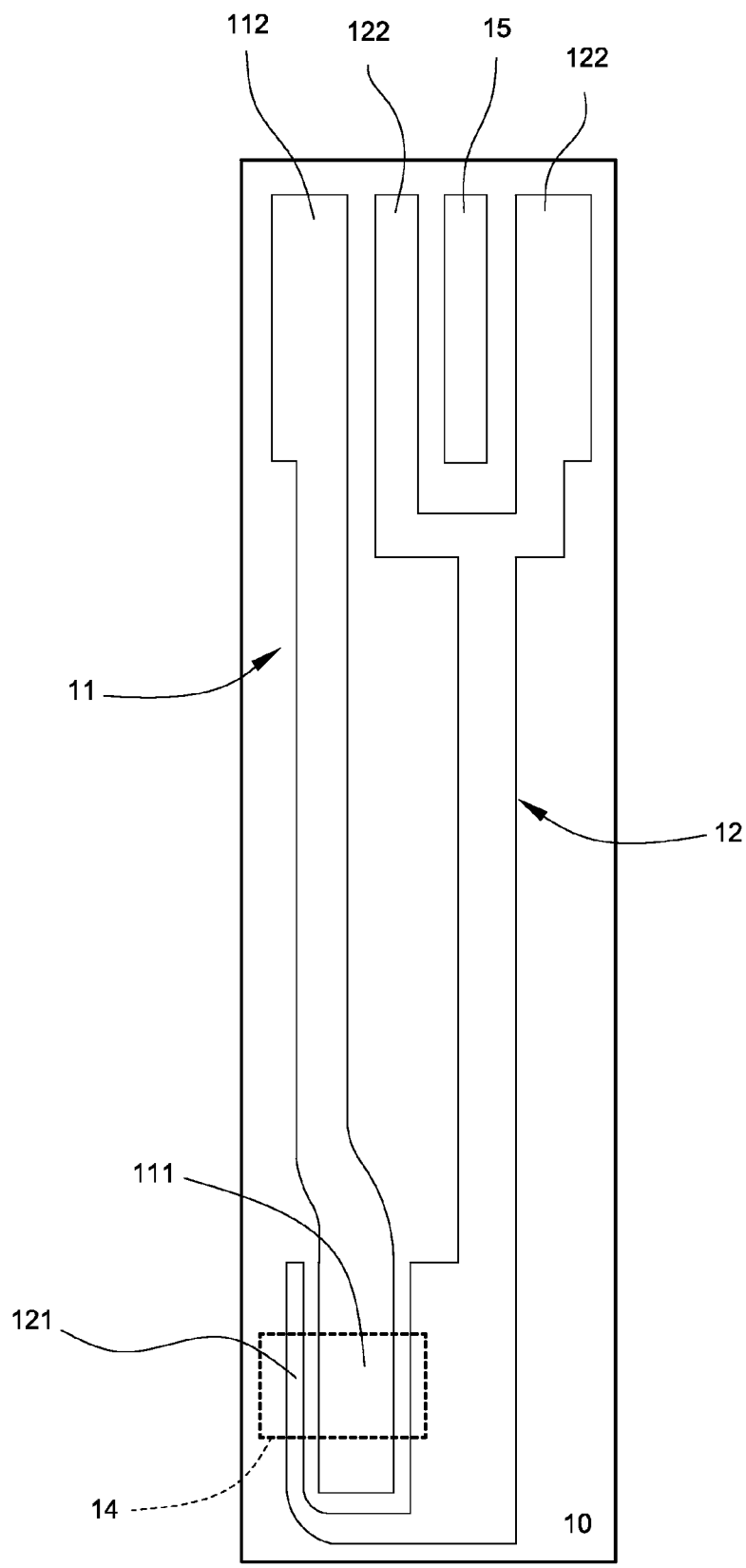
FIG. 6 shows another arrangement of the wires.
Figure 7:
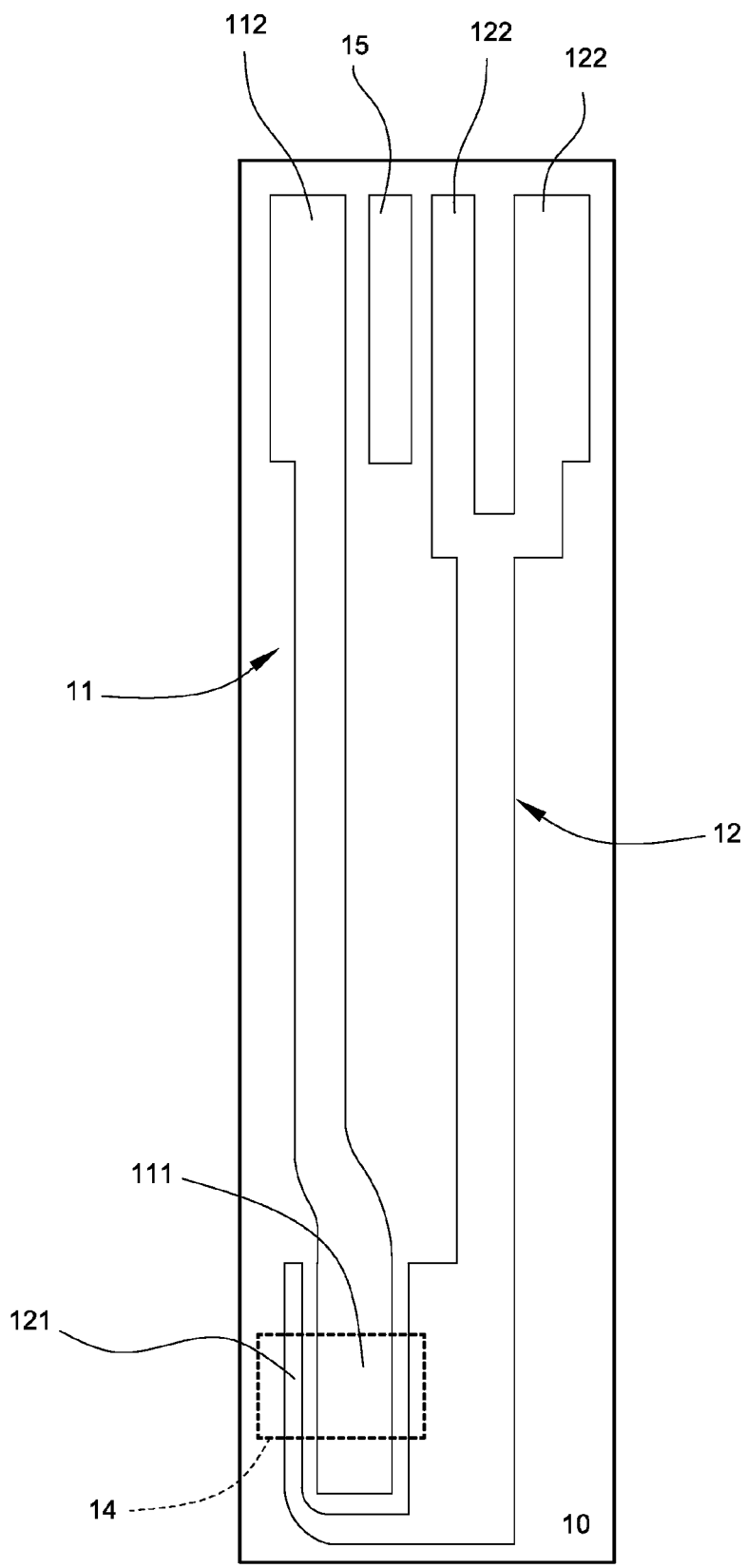
FIG. 7 shows still arrangement of the wires.
Figure 8:
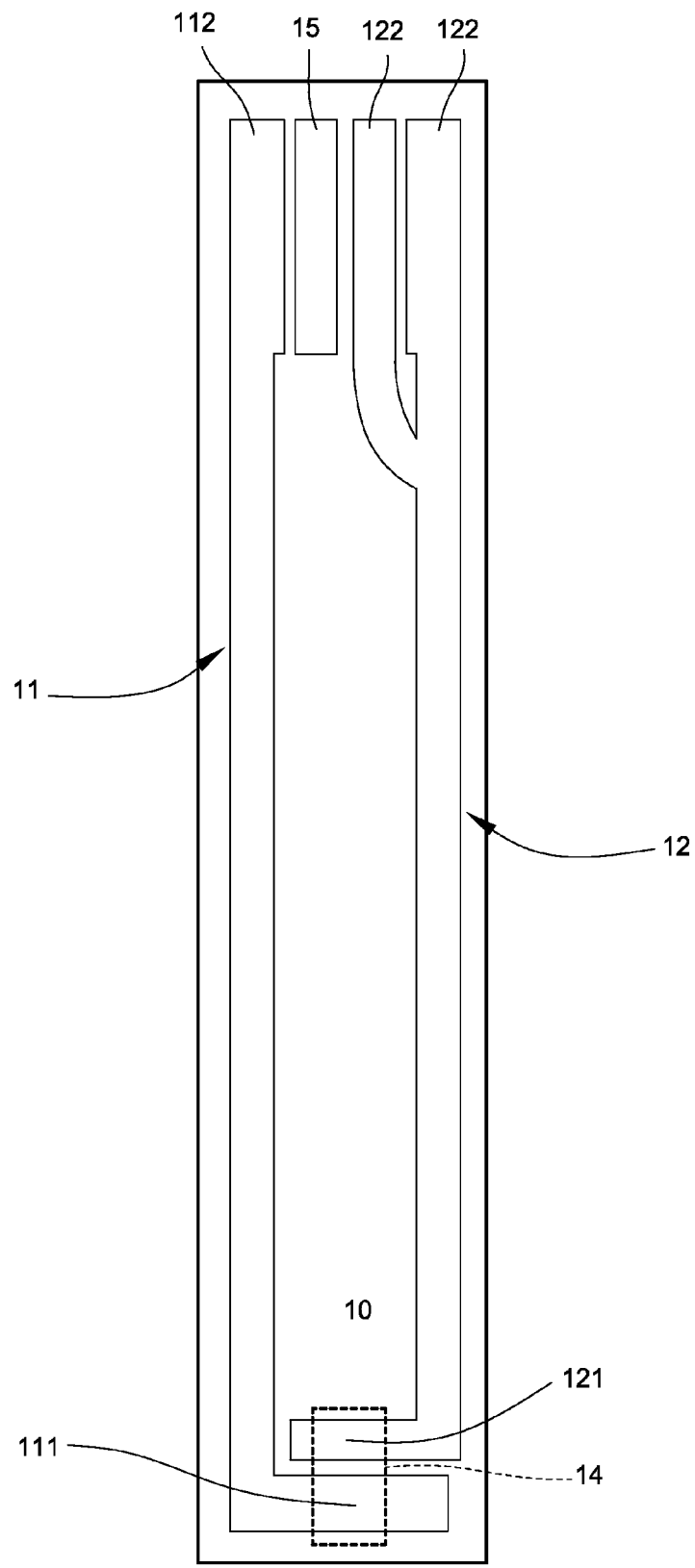
FIG. 8 shows yet arrangement of the wires.

Please refer to FIG. 5. The working wire 11 and grounding wire 12 may be arranged into different shapes to match various biosensors. FIG. 5 depicts the first arrangement of the working wire 11 and grounding wire 12. FIGS. 6-8 depict another three arrangements of the working wire 11 and grounding wire 12. In each of these arrangements, a disconnected wire 15 is introduced. The disconnected wire 15 can provide a signal parameter for discrimination of different test strips.

Figure 9:
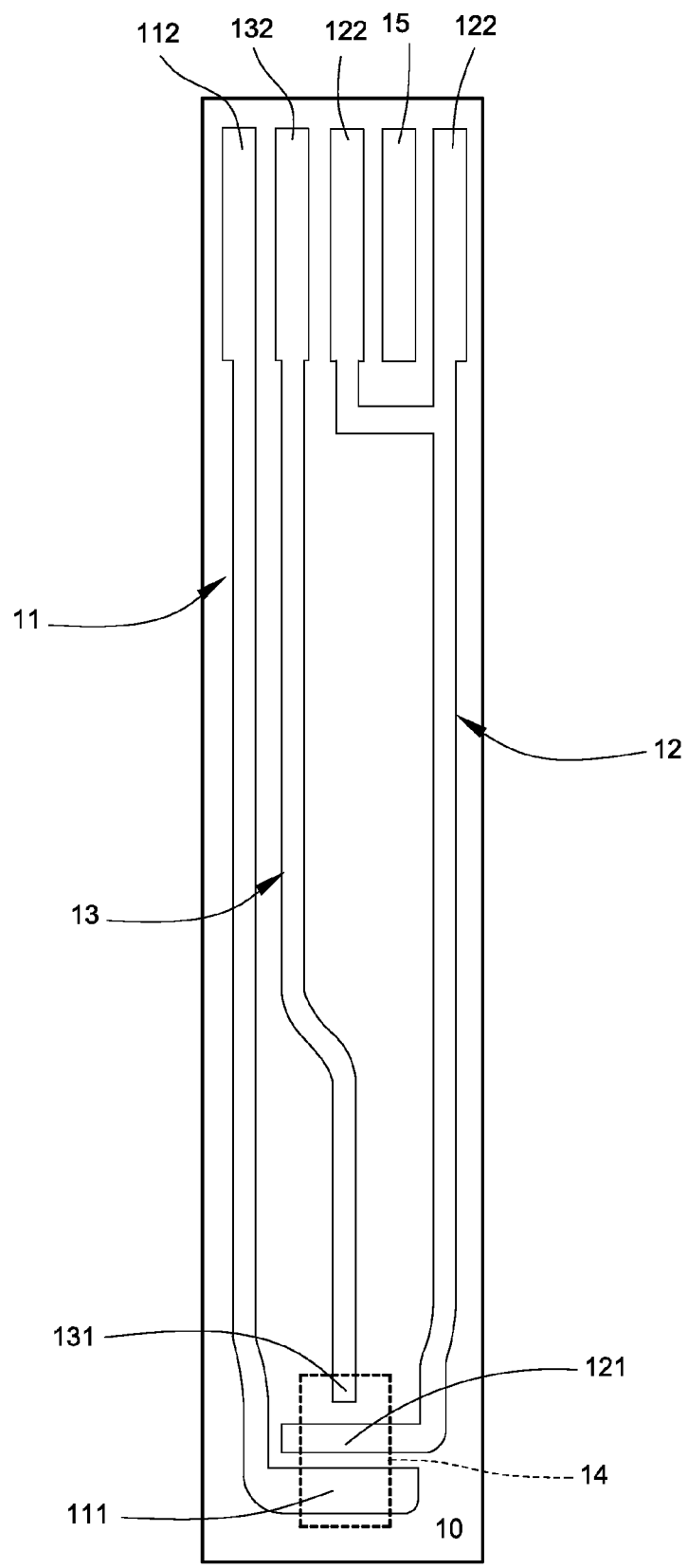
FIG. 9 shows an arrangement of the wires with a sample detection wire.
Figure 10:
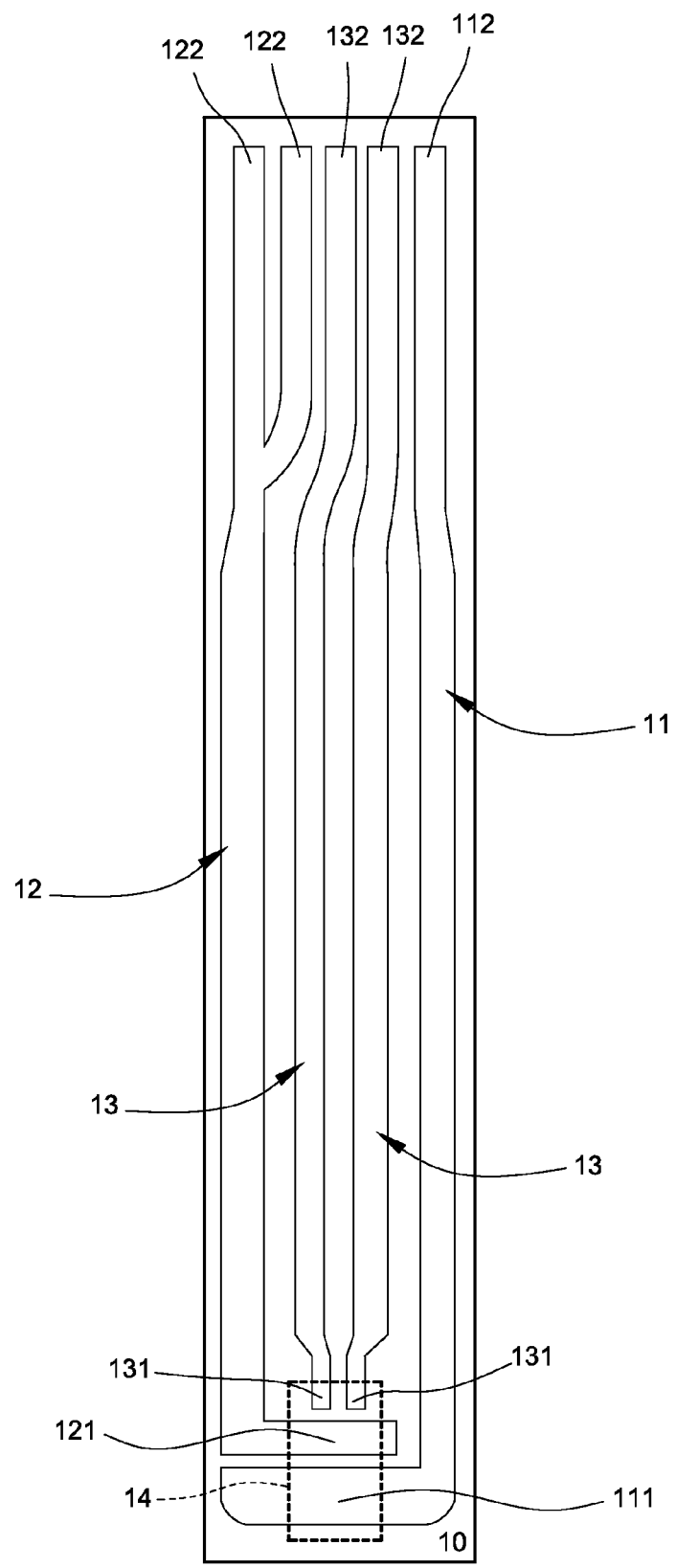
FIG. 10 shows another arrangement of the wires with a sample detection wire.
Figure 11:
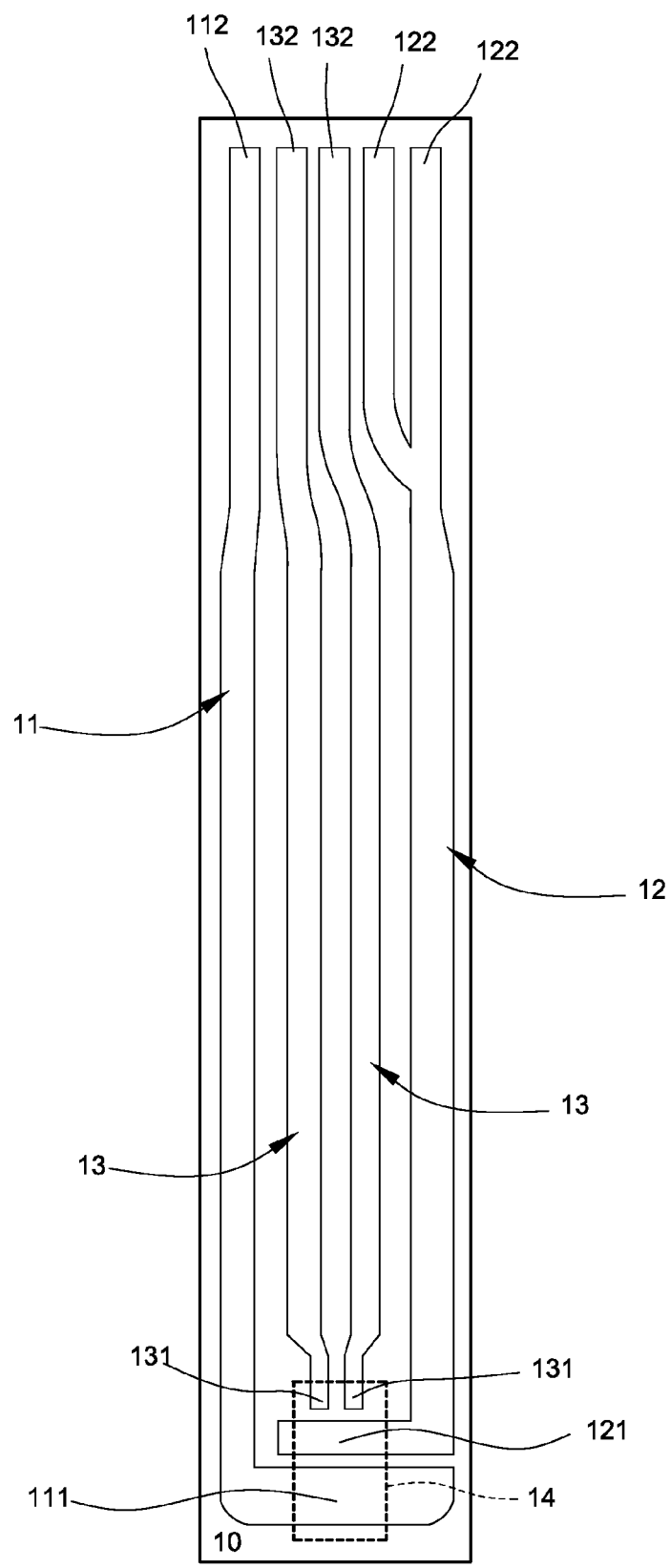
FIG. 11 shows still arrangement of the wires with a sample detection wire.

FIGS. 9, 10 and 11 depict other wiring arrangements of the invention. A sample detection wire 13 is further introduced. Two ends of the sample detection wire 13 are separately formed with a third measure contact 132 and a third bioreaction contact 131 extending into the reaction area 14. When the sample is insufficient or not located in a correct position, the sample detection wire 13 can output a signal to reflect.

Figure 12:
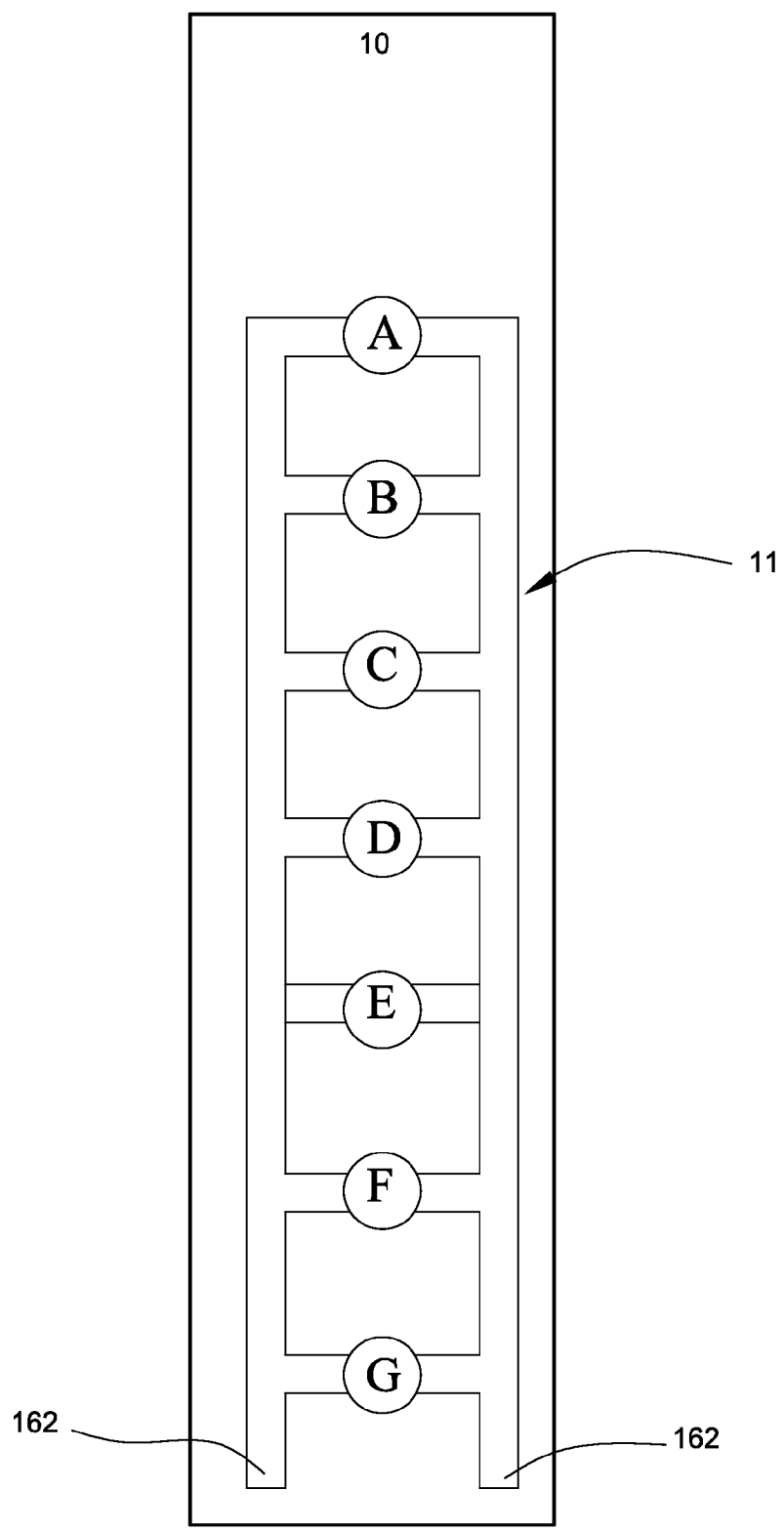
FIG. 12 shows the code wire of the invention.

The embodiment shown in FIG. 12 further introduces a code wire 16. The code wire 16 is formed on the base 10, and the code wire 16 and the working and grounding wires 11, 12 are separately located on two opposite sides of the base 10. An end of the code wire 16 is formed with a plurality of fourth measure contacts 162 for connecting a biosensor.

Figure 13:
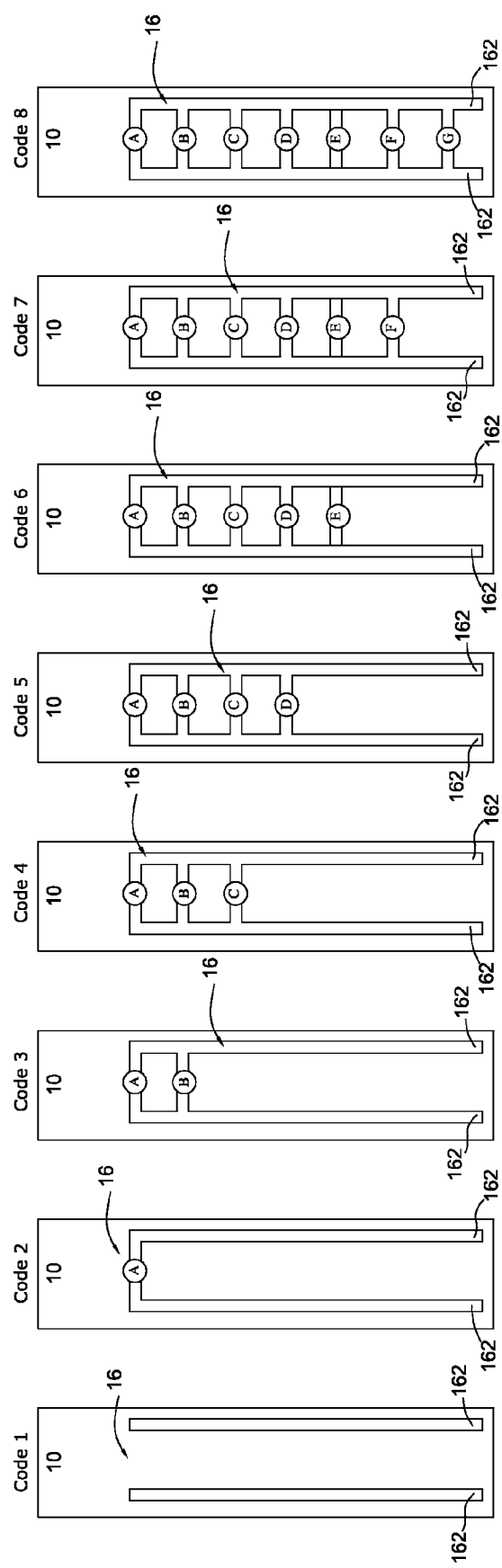
FIG. 13 shows variations of the code wire of the invention.

Please refer to FIG. 13. The code wire 16 may contain different codes, for example, codes 1, 2, 3, 4, 5, 6, 7 and 8 are appointed by 0, 1, 2, 3, 4, 5, 6, 7 nodes A, B, C, D, E, F and G between two lines of the code wire 16, respectively. Because different types of test strips must use distinct codes implemented by the number of the nodes, the number of the nodes can be used to distinguish different test strips. In other words, when a test strip of the invention is inserted into a biosensor, the biosensor can know the type of the test strip inserted by the codes.

When a specimen is injected in the guiding trough 50, the specimen will be promote to flow by the air passage 50. And the specimen can be checked through the transparent cover layer 40 until the required amount has been reached. The specimen on the reaction area 14 can be tested through bioelectricity.

The test strip which is inserted into a biosensor will make an electrical connection therebetween. The biosensor will supply electrical signals to the test strip and obtain resultant signals to display.

It will be appreciated by persons skilled in the art that the above embodiments have been described by way of example only and not in any limitative sense, and that various alterations and modifications are possible without departure from the scope of the invention as defined by the appended claims.

What is claimed is:

1. A test strip comprising:
    a base, having a reaction area;
    a working wire, formed on the base, two ends thereof being separately formed with a first measure contact and a first bioreaction contact, and the first bioreaction contact extending into the reaction area;
    a grounding wire, formed on the base, parallel to the working wire, two ends thereof being separately formed with a second measure contact and a second bioreaction contact, and the second bioreaction contact extending into the reaction area;
    a first division layer having a first inlet, wherein the first inlet is formed by indenting a portion of one linear edge of the first division layer;
    a second division layer, being a single piece without any separation, having a second inlet, superposed on the first division layer, overlapped with the working wire and the grounding wire, and being provided with an air passage trough directly communicating and connecting with the second inlet, wherein the second inlet is formed by indenting a portion of one linear edge of the second division layer, the first inlet and the second inlet correspond to the reaction area in position to expose the first and second bioreaction contacts, and the air passage trough is a bottomed recess; and
    a cover layer, attached on the second division layer, and completely cloaking one side of the second division layer, wherein a guiding trough is formed by the cover layer, the base and the first and second inlets;
    wherein the reaction area is coated with a bioreaction film, the air passage trough is perpendicular to the second inlet, a disconnected wire is disposed on the base, two ends of a sample detection wire are separately formed with a third measure contact and a third bioreaction contact extending into the reaction area, an adhesive layer is disposed between the first division layer and the base, the adhesive layer is formed with a recess corresponding to the first inlet, and the adhesive layer is made of polyethylene terephthalate (PET), and an end of the code wire is formed with a plurality of fourth measure contacts.

2. The test strip of claim 1, wherein the code wire is composed of two parallel lines.

3. The test strip of claim 1, wherein the code wire further comprises at least one node.

4. The test strip of claim 3, wherein the code wire further comprises two or more nodes.

* * * * *